United States Patent [19]

Misevich

[11] Patent Number: 5,168,634

[45] Date of Patent: Dec. 8, 1992

[54] UNIVERSAL PLATFORM

[75] Inventor: Kenneth W. Misevich, Moosup, Conn.

[73] Assignee: Colgate-Palmolive Company, Piscataway, N.J.

[21] Appl. No.: 720,368

[22] Filed: Jun. 25, 1991

[51] Int. Cl.⁵ .......................................... A61B 5/103
[52] U.S. Cl. ...................................... 33/515; 33/512; 128/779
[58] Field of Search ............... 33/512, 511, 515, 3 B, 33/3 C; 128/774, 779; 73/172

[56] References Cited

U.S. PATENT DOCUMENTS

| | | | |
|---|---|---|---|
| 3,134,591 | 5/1964 | Conn, Jr. et al. | |
| 3,587,296 | 6/1971 | Povoas | |
| 4,062,355 | 12/1977 | Kaye | 128/25 |
| 4,199,137 | 4/1980 | Giguere | 272/96 |
| 4,201,226 | 5/1980 | Phillips | 128/774 |
| 4,306,571 | 12/1981 | McLeod, Jr. | 128/782 |
| 4,416,292 | 11/1983 | Brown | 128/779 |
| 4,452,447 | 6/1984 | Lepley et al. | 272/96 |
| 4,461,085 | 7/1984 | Dewar et al. | |
| 4,517,696 | 5/1985 | Schartz | 128/779 |
| 4,605,224 | 8/1986 | Torii | 272/146 |
| 4,618,145 | 10/1986 | Inada | 272/146 |
| 4,629,181 | 12/1986 | Krive | 272/97 |
| 4,771,548 | 9/1988 | Donnery | 33/512 |
| 4,794,706 | 1/1989 | Puckhaber et al. | 36/91 |
| 4,802,494 | 2/1989 | Gardiner | 128/779 |
| 4,860,464 | 8/1989 | Misevich et al. | 36/114 |

FOREIGN PATENT DOCUMENTS 8802236 4/1988 World Int. Prop. O. .......... 128/779

Primary Examiner—William A. Cuchlinski, Sr.
Assistant Examiner—William C. Dowling
Attorney, Agent, or Firm—Nies, Kurz, Bergert & Tamburro

[57] ABSTRACT

Apparatus for measuring the loaded axes of the foot is disclosed. The apparatus is particularly well suited for location of the ankle (talo-crural) and subtalar (talo-calcaneal) joint axes. The apparatus inludes a platform having one major axis of rotation to which either the ankle or subtalar axes can be aligned. The platform is hung from this fuxture axis and has adjustment for both height and pitch. The platform is adjustable from side to side and rotates about the perpendicular to the hanging support.

2 Claims, 4 Drawing Sheets

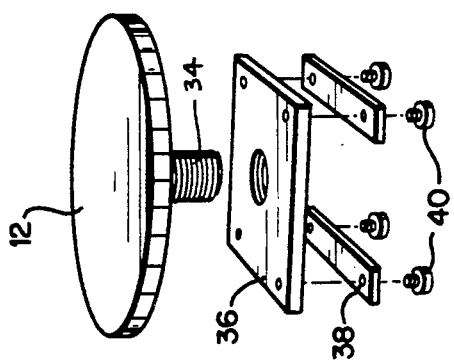
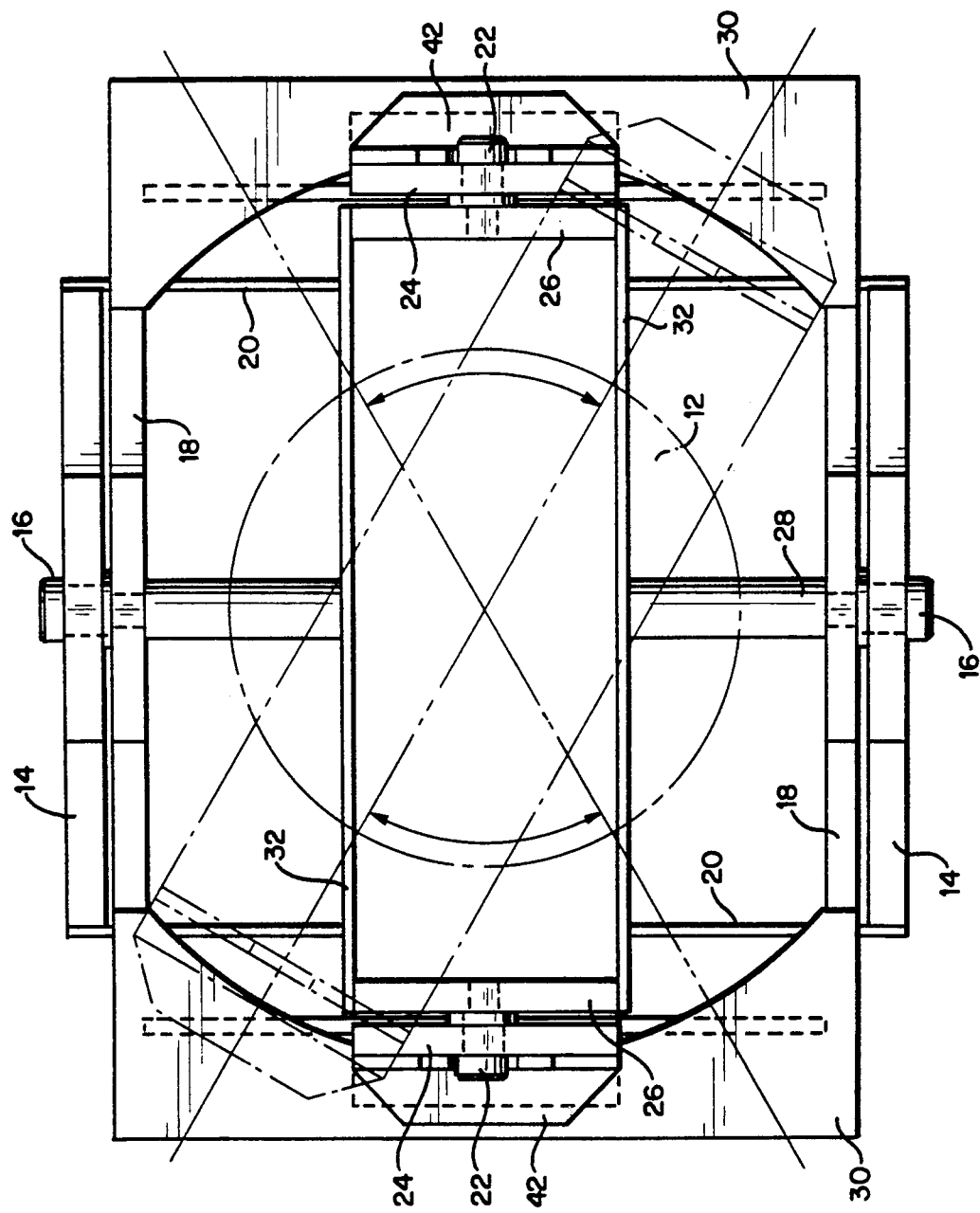

UNIVERSAL PLATFORM

BACKGROUND AND SUMMARY OF THE INVENTION

The present invention relates to a device for measurement of body motion. More particularly, the present invention relates to a platform assembly for use in measuring the loaded axes of the foot.

Apparatus such as goniometers have been known in the art for measuring the ranges of motion of body joints. However, no prior apparatus has been available commercially for measuring the loaded joints of the foot when loaded with full body weight in an in vivo condition.

By the present invention, there is provided a universal platform device on which the ankle (talo-crural) and subtalar (talo-calcaneal) joint axes can be located in the weight bearing foot. The device of the present invention provides simple effective biofeedback, i.e., rotation of a joint without other forces or motion on the leg, to aid the subject with the result that the device is extremely easy to use.

The platform assembly device of the present invention allows rotation of the above described joint axes about an aligned fixture axis in order to study the functions of the foot including measurements of the ranges of motion of the axes.

Since previously there was no commercially available means of measuring the loaded axes of the foot, a fixture was required to be designed and constructed to carry out such measurements. The universal platform of the present invention allows an internal axis to be determined by lining up the machine axis with an anatomical axis. By monitoring the leg motion while rotating the platform, the machine is adjusted so that the two axes are co-linear. When the axes are aligned, the universal platform can be rotated without causing leg motion. In this manner, the hypothesis which holds that only the talo-calcaneal joint behaves as a true axis under load can be proved.

BRIEF DESCRIPTION OF THE DRAWINGS

FIG. 2 is a top plan view of the universal platform of FIG. 1.

FIG. 8 is an exploded perspective view of a platform installation unit employed in the platform assembly of FIG. 1.

DESCRIPTION OF THE PREFERRED EMBODIMENTS

Figure 1:
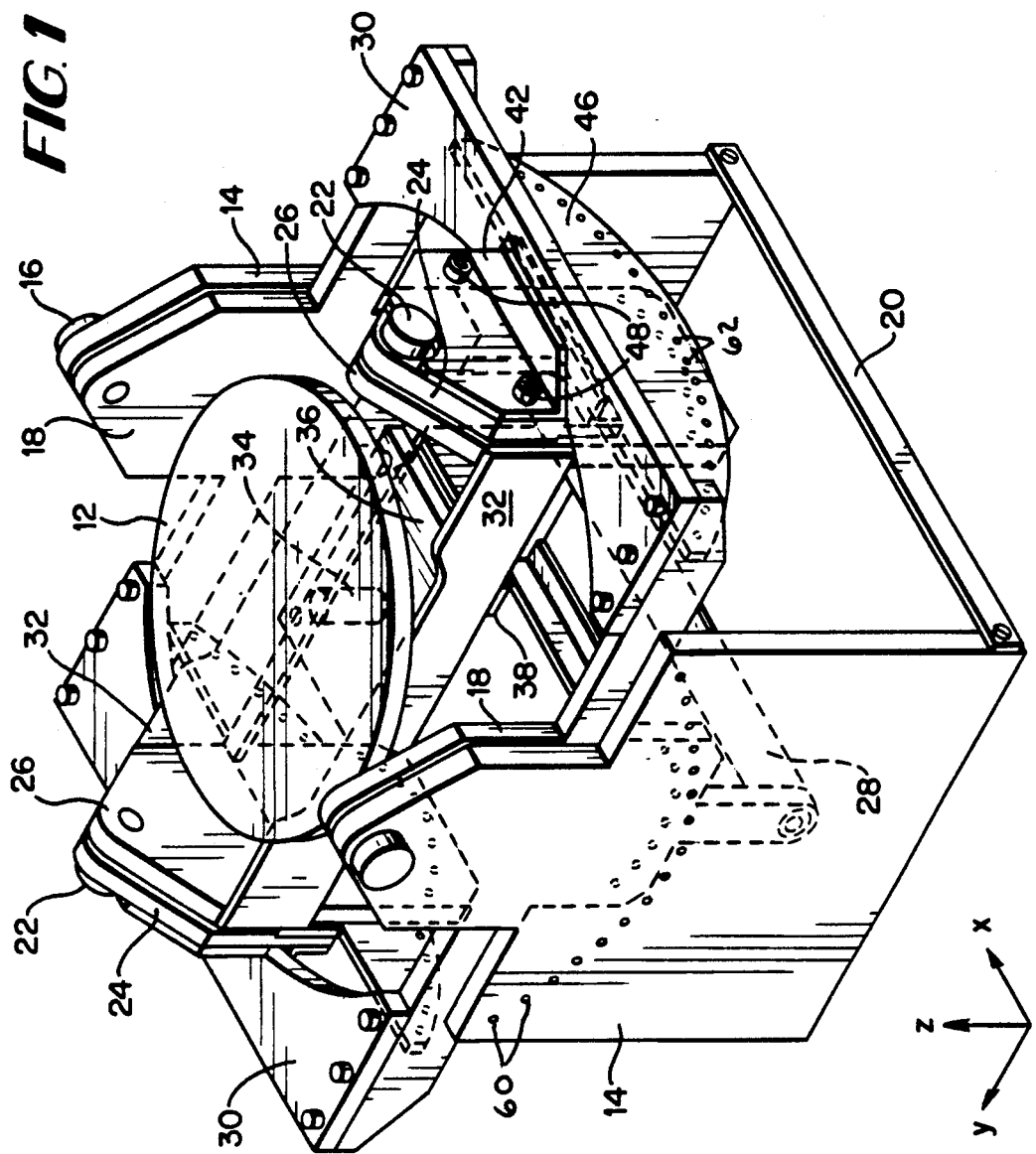
FIG. 1 is a perspective view of the universal platform assembly of the present invention.

In the embodiment of the present invention as shown in FIGS. 1 through 8, there is provided a platform device 10 for use in measuring the axes of the foot.

The platform device 10 includes a platform member 12 rotatably mounted in main vertical support plates 14 by pins 16 which extend in an x-axis direction. A pair of x-axis vertical support plates 18 are rotatably mounted interiorly of the respective main support plates 14. A pair of x-axis side plates 30 are mounted at opposite ends of the vertical plates 18. The side plates 30 provide a base for mounting a pair of main y-axis support plates 24 which are secured to the respective side plates 30 by upper y-axis brackets 42.

A pair of interior support plates 26 are rotatably mounted on support plates 24 by y-axis pins 22. A pair of y-axis side plates 32 are secured to and extend between the interior side plates 26.

As shown in FIGS. 1 and 8, the platform 12 is mounted in z-axis support plate 36 by means of a threaded shaft 34 welded or otherwise fixed to the bottom of the platform 12 so as to allow the platform 12 to be raised and lowered. The support plate 36 is secured to the side plates 32 by means of a pair of clamping bars 38 and bolts 40.

Figure 6:
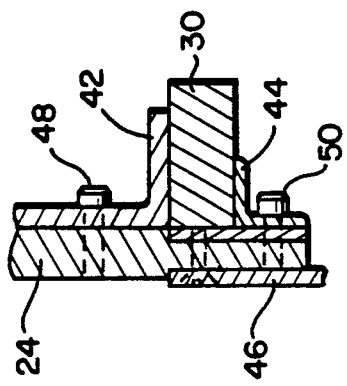
FIG. 6 is a cross-sectional view taken along line 6-6 of FIG. 4.

The main y-axis support plates 24 are secured to the respective side plates 30 by the use of upper 42 and lower 44 y-axis brackets attached by upper 48 and lower 50 securing bolts, as shown in FIG. 6. A y-axis locking plate 46 is employed to allow the y-axis to be locked in the desired position.

Figure 7:
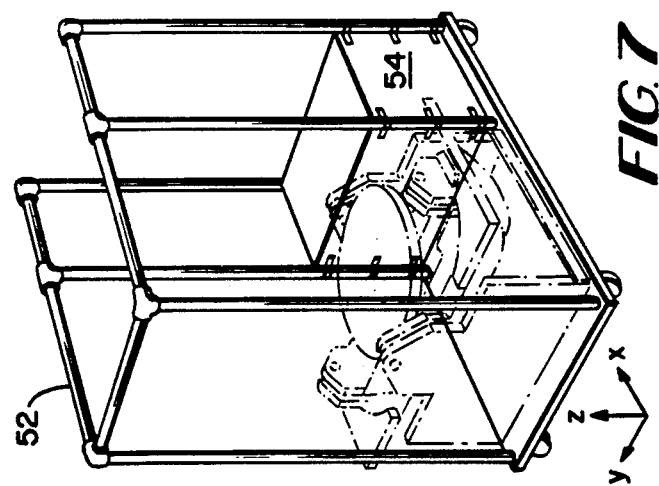
FIG. 7 is a perspective view of the universal platform of the invention as employed with a stabilizing assembly for measuring the axes of the feet.

In FIG. 7 there is shown a rail support structure 52 which may be employed for use in mounting the present platform device 10 to allow a person using the device 10 to maintain a stable position. A foot support box 54 is mounted on the rail structure 52 to provide a platform for one foot of the operator while the other foot is positioned on the platform 12.

All components connected with pins 16 or 22 are freely rotatable. The alignment of the x, y and z axes is as shown in FIG. 7, facing in the y-axis direction.

The platform device of the present invention is particularly useful in locating the talo-calcaneal axis. This device 10 provides the only known means by which this axis can be measured under load and such a measurement is critical to the correct theoretical modeling of the structural foot.

The universal platform 10 of the present invention has one major axis of rotation to which either the ankle or subtalar axes can be aligned. The platform 12 is hung from this fixture axis and has adjustment for both height and pitch. The platform 12 is adjustable from side to side in the y direction and rotates about the perpendicular to the hanging support.

Figure 3:
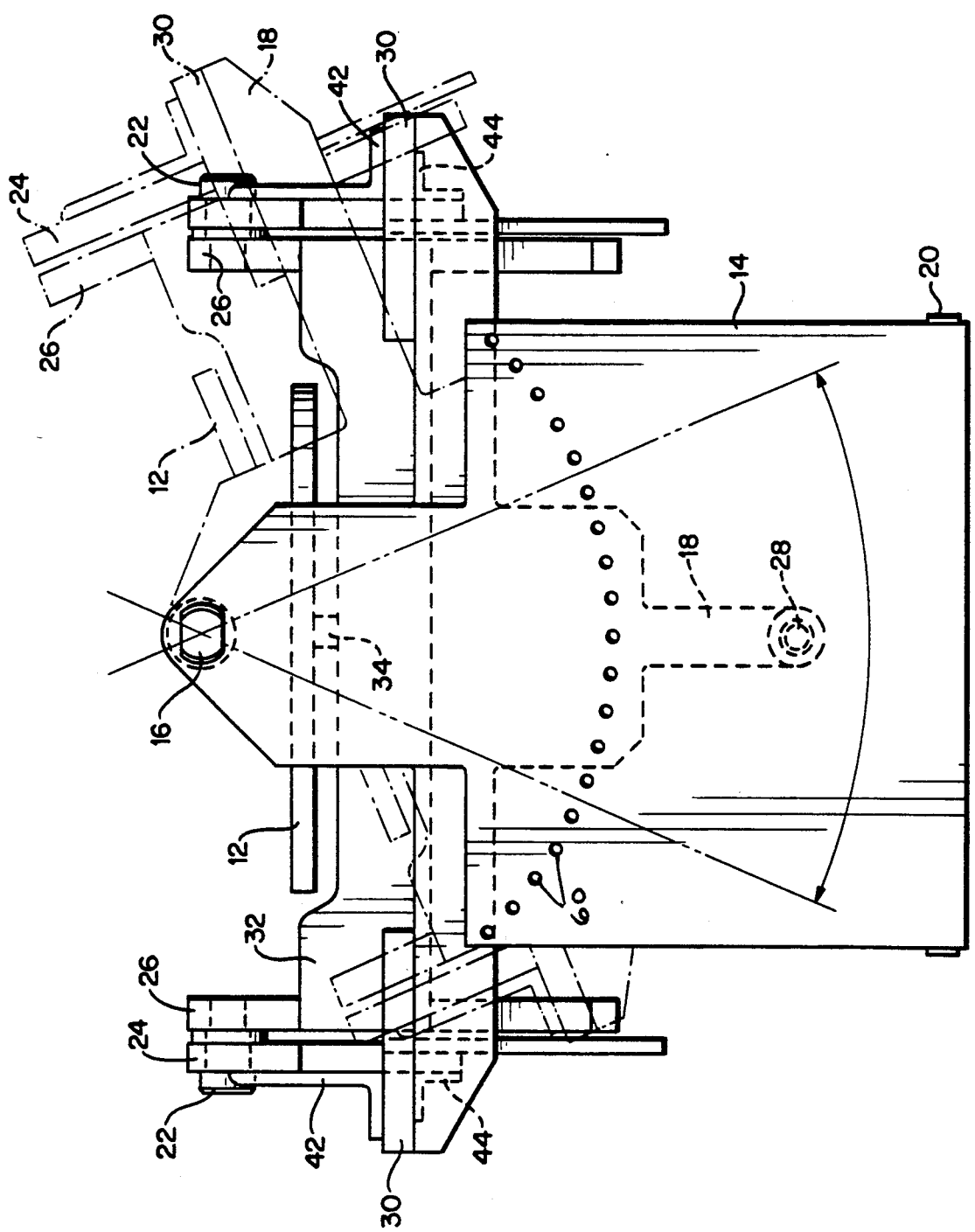
FIG. 3 is a side elevation of the universal platform of FIG. 1.
Figure 5:
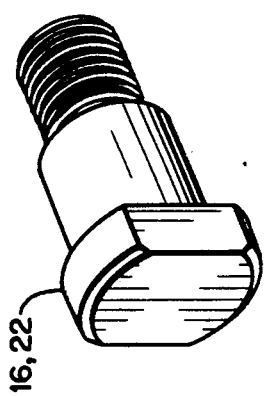
FIG. 5 is a perspective view of the pin member employed with the universal platform of FIG. 1.
Figure 4:
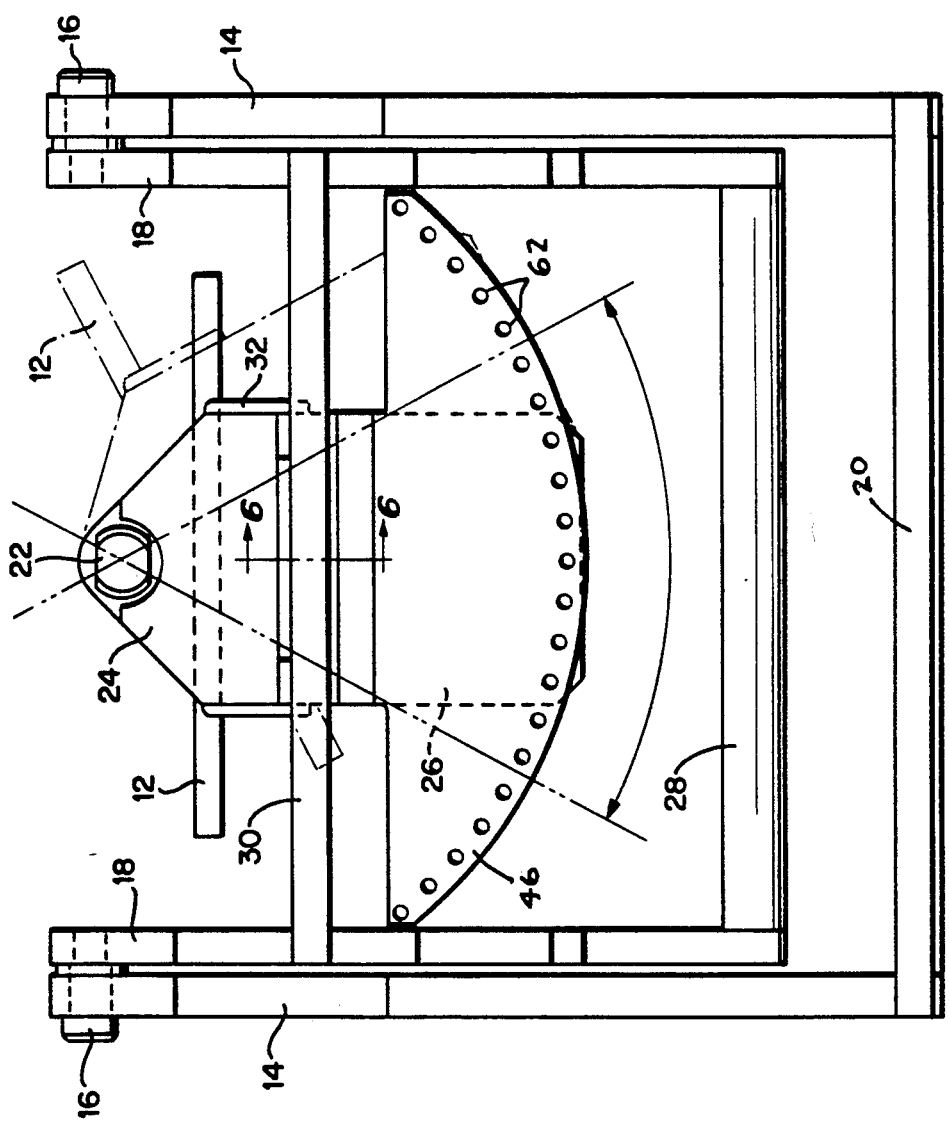
FIG. 4 is an end elevation of the universal platform of FIG. 1.

As shown in FIGS. 1, 3 and 4, plates 14 and 46 are provided with holes 60 and 62 respectively for use in receiving pins which allow the device to be fixed at the desired angle. In one embodiment, these holes 60, 62 are arranged at intervals of 10 degrees in an arc along the respective plates 14 and 46.

A basic concept of the present invention is to provide for continuous rotation of the foot about either of its axes until there is no motion of the leg. When no further leg motion occurs, the axis is aligned with the fixture and its spatial position is then known.

The spatial adjustments include the following:
(1) height and pitch relative to major fixture axis.
(2) vertical rotation or yaw with respect to the axis.
(3) small vertical translation.

It has been found that only the degrees of freedom of the fixture are important. Design details will only affect the ease of utilization. Further, the method of gauging the final spatial position of the foot is arbitrary and can be carried out either by the use of protractor scales, a visual reading or any of a number of electrical transducers. The employment of visual or audible biofeedback to the subject or operator is arbitrary and will only enhance the ease of use of the invention.

An important advantage of the present invention over the prior art resides in the fact that, while the position of the talo-calcaneal axis has been known, as described for example in U.S. Pat. Nos. 4,794,706 and 4,860,464, there has heretofore not been a practical way to measure this position. Now, by the use of the universal platform of the present invention, a precise indication of the location of this axis can be provided.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be obtained by Letters Patent is:

1. Apparatus for measuring the loaded axes of the foot, comprising:
    a first frame member having a pair of exterior vertical side plates;
    a first pair of interior vertical side plates, each of said first pair of interior vertical side plates being rotatably mounted to a respective exterior vertical side plate by a pin member which extends in a first horizontal direction;
    a second frame member which connects opposite ends of said first pair of interior vertical side plates;
    a second pair of interior vertical side plates, each of said second pair of vertical side plates being rotatably mounted to a respective end portion of said second frame member by a pin member which extends in a second horizontal direction which is perpendicular to said first horizontal direction;
    a third frame member which connects opposite ends of said second pair of vertical side plates;
    means for fixing the position of said first pair of interior vertical side plates at a predetermined angle relative to said exterior vertical side plates;
    means for fixing the position of said second pair of interior vertical side plates at a predetermined angle relative to said second frame member;
    means for measuring the positions of said first and second pair of interior vertical side plates;
    means for rotatably mounting a horizontal foot supporting platform to said second frame member; and
    means for raising and lowering said platform.

2. The apparatus of claim 1 wherein said platform is rotatable about a vertical axis.

* * * * *